(12) United States Patent
Manimaran et al.

(10) Patent No.: US 6,313,355 B1
(45) Date of Patent: Nov. 6, 2001

(54) PROCESS FOR THE PREPARATION OF TETRABROMOBISPHENOL-A

(76) Inventors: Thanikavelu Manimaran, 1623 Plantation Oaks Dr., Baton Rouge, LA (US) 70810; Richard A. Holub, 6638 Millstone Dr., Baton Rouge, LA (US) 70808; Randall S. Barton, 12742 Lazy K Ave., Baton Rouge, LA (US) 70810

( * ) Notice: Subject to any disclaimer, the term of this patent is extended or adjusted under 35 U.S.C. 154(b) by 0 days.

(21) Appl. No.: 09/614,819

(22) Filed: Jul. 12, 2000

Related U.S. Application Data

(63) Continuation of application No. 09/416,855, filed on Oct. 12, 1999, which is a continuation-in-part of application No. 09/329,374, filed on Jun. 10, 1999, which is a continuation-in-part of application No. 09/096,332, filed on Jun. 11, 1998, now Pat. No. 6,084,136, and a continuation-in-part of application No. 08/945,158, filed on Oct. 21, 1997, now Pat. No. 6,084,137, said application No. 09/096,332, filed on Jun. 11, 1998, now Pat. No. 6,084,136, is a continuation-in-part of application No. 08/945,158, filed on Oct. 21, 1997, now Pat. No. 6,084,137, which is a continuation-in-part of application No. 08/426,996, filed on Apr. 24, 1995, now abandoned, and a continuation-in-part of application No. 08/426,998, filed on Apr. 24, 1995, now abandoned, which is a continuation-in-part of application No. 08/398,837, filed on Mar. 6, 1995, now abandoned, said application No. 08/945,158, filed on Oct. 21, 1997, now Pat. No. 6,084,137, is a continuation-in-part of application No. 08/550,044, filed on Oct. 30, 1995, now Pat. No. 5,723,690, which is a continuation of application No. 08/426,997, filed on Apr. 24, 1995, now Pat. No. 5,527,971.

(51) Int. Cl.$^7$ .................................................. C07C 39/16
(52) U.S. Cl. .................. 568/726; 568/721; 568/722; 568/723; 568/724; 568/725; 568/774; 568/776; 568/779
(58) Field of Search ................................ 568/726, 721, 568/722, 723, 724, 725, 774, 776, 779

(56) References Cited

U.S. PATENT DOCUMENTS

| | | | |
|---|---|---|---|
| 2,455,652 | 12/1948 | Bralley et al. | 260/77.5 |
| 3,029,291 | 4/1962 | Dietzler | 260/619 |
| 3,143,575 | 8/1964 | Bryner et al. | 260/619 |
| 3,182,088 | 5/1965 | Hennis | 260/619 |
| 3,234,289 | 2/1966 | Hennis | 260/619 |
| 3,363,007 | 1/1968 | Majewski et al. | 260/619 |
| 3,546,302 | 12/1970 | Asadorian et al. | 260/619 |
| 3,868,423 | 2/1975 | Montanari et al. | 260/619 A |
| 3,929,907 | 12/1975 | Janzon et al. | 260/619 R |
| 4,013,728 | 3/1977 | Brackenridge | 260/619 A |
| 4,036,894 | 7/1977 | Jenkner | 260/619 A |

(List continued on next page.)

FOREIGN PATENT DOCUMENTS

| | | |
|---|---|---|
| 686772 | 5/1964 | (CA) . |
| 706433 | 3/1965 | (CA) . |
| 2041220 | 3/1971 | (DE) . |
| 3417027 | 11/1985 | (DE) . |
| 0367869 | 5/1990 | (EP) . |
| 0380363 | 8/1990 | (EP) . |
| 0380365 | 8/1990 | (EP) . |
| 0472395 | 2/1992 | (EP) . |
| 0572154 | 12/1993 | (EP) . |
| 0574031 | 12/1993 | (EP) . |

(List continued on next page.)

OTHER PUBLICATIONS

Chemical Abstracts vol. 78, 1973, p. 328.
Chemical Abstracts vol. 96, 1982, p. 718.
Chemical Abstracts vol. 104, 1986, p. 656.
Chemical Abstracts vol. 104, 1986, p. 716.
Islam et al., "Tetrahalogenated 4:4'–Dihydroxydiphenylalkanes, their Synthesis and some of their Reactions", Egypt J. Chem., vol. 20, No. 5, 1977, ppg. 483–490.
Sadygov et al., "Oxidative Bromination of 2,2–Bis(4'–Hydroxyphenyl) Propane", Neftekhimiya, vol. 30, No. 1, 1990, ppg. 109–113. (Translation attached p. 1–7).
Patent Abstracts of Japan, Publication No. JP 62048641, Publication Date Mar. 3, 1987, entitled "Bromination of Bisphenol Compound".
Levenspiel Chemical Reaction Eng. (1962), Chapter 6, p. 126, 1962.
Chemical Abstract, vol. 86, 1977, ppg. 570, JP 77,05745.
CAPLUS, Abstract of JP 52,034620, 1977.
WPIDS, Abstract of JP 77/034620, 1977.
JAPIO, Abstract of JP 52,005745, 1977.

*Primary Examiner*—Sreeni Padmanabhan

(57) ABSTRACT

Tetrabromobisphenol-A is produced in a bromination process where no bromine or only a very small proportion of bromine is fed to the reactor. In the process aqueous hydrobromic acid, is the sole source or a major source of the bromine. In the process there are at least three concurrent continuous feeds to the reactor. One is composed of bisphenol-A and/or underbrominated bisphenol-A and a water-miscible organic solvent. The second is gaseous hydrogen bromide or preferably, aqueous hydrobromic acid, and the third is aqueous hydrogen peroxide. Optionally a small additional continuous feed of bromine can be employed. The feeds are proportioned to maintain a liquid phase containing (i) from above about 15 to about 85 wt % water, based upon the amount of water and water-miscible organic solvent in such liquid phase, and (ii) an amount of unreacted bromine that is in excess over the stoichiometric amount theoretically required to convert the bisphenol-A and/or underbrominated bisphenol-A to tetrabromobisphenol-A. The tetrabromobisphenol-A continuously forms as a solids phase in a yield of at least about 90% based on bisphenol-A and/or underbrominated bisphenol-A fed. The reaction mass is agitated and/or refluxed to maintain a substantially uniform slurry in the reactor. An amount of the slurry is continuously removed so that the volume of the contents of the reactor remains substantially constant.

14 Claims, No Drawings

U.S. PATENT DOCUMENTS

| | | | |
|---|---|---|---|
| 4,112,242 | 9/1978 | Swietoslawski et al. | 568/726 |
| 4,180,684 | 12/1979 | Kleinschmit et al. | 568/726 |
| 4,282,391 | 8/1981 | Quinn et al. | 568/726 |
| 4,283,566 | 8/1981 | Mark | 568/726 |
| 4,291,177 | 9/1981 | Mark et al. | 568/726 |
| 4,302,614 | 11/1981 | Dannenberg et al. | 568/641 |
| 4,451,675 | 5/1984 | Bounds | 568/726 |
| 4,628,124 | 12/1986 | McKinnie et al. | 568/726 |
| 4,692,555 | 9/1987 | Shin | 568/722 |
| 4,701,568 | 10/1987 | McKinnie et al. | 568/726 |
| 4,783,556 | 11/1988 | Mitchell et al. | 568/726 |
| 4,909,997 | 3/1990 | Mitchell et al. | 422/225 |
| 4,990,321 | 2/1991 | Sato et al. | 423/486 |
| 5,008,469 | 4/1991 | Eguchi et al. | 568/722 |
| 5,017,728 | 5/1991 | McKinnie et al. | 568/726 |
| 5,059,722 | 10/1991 | Mitchell et al. | 568/226 |
| 5,059,726 | 10/1991 | Eguchi et al. | 568/726 |
| 5,068,463 | 11/1991 | Walter | 568/726 |
| 5,107,035 | 4/1992 | Hines et al. | 568/726 |
| 5,138,103 | 8/1992 | Eguchi et al. | 568/726 |
| 5,208,389 | 5/1993 | McKinnie et al. | 568/726 |
| 5,237,112 | 8/1993 | LaRose | 568/726 |
| 5,283,375 | 2/1994 | McKinnie et al. | 568/726 |
| 5,302,761 | 4/1994 | Tambayashi et al. | 568/726 |
| 5,446,212 | 8/1995 | Sanders et al. | 568/726 |
| 5,527,971 | 6/1996 | McKinnie | 568/726 |
| 5,723,690 | 3/1998 | McKinnie | 568/726 |
| 5,847,232 | 12/1998 | McKinnie | 568/726 |
| 6,002,050 | 12/1999 | McKinnie | 568/726 |

FOREIGN PATENT DOCUMENTS

| | | |
|---|---|---|
| 2274586 | 1/1976 | (FR) . |
| 949306 | 2/1964 | (GB) . |
| 1031500 | 6/1966 | (GB) . |
| 1316415 | 5/1973 | (GB) . |
| 64410 | 11/1981 | (IL) . |
| 58-225034 | 12/1983 | (JP) . |
| 60-58728 | 12/1985 | (JP) . |
| 62-48641 | 3/1987 | (JP) . |
| 63-316748 | 12/1988 | (JP) . |
| 2196747 | 8/1990 | (JP) . |
| 4099743 | 3/1992 | (JP) . |
| 5229976 | 1/1993 | (JP) . |
| 5213804 | 8/1993 | (JP) . |
| 2026280 | 1/1995 | (SU) . |
| 9611227 | 4/1996 | (WO) . |
| 9620911 | 7/1996 | (WO) . |
| 9627576 | 9/1996 | (WO) . |
| 9633964 | 10/1996 | (WO) . |

PROCESS FOR THE PREPARATION OF TETRABROMOBISPHENOL-A

REFERENCE TO RELATED APPLICATIONS

This application is a continuation of commonly-owned copending U.S. application Ser. No. 09/416,855, filed Oct. 12, 1999, the latter application being a continuation-in-part of commonly-owned copending U.S. application Ser. No. 09/329,374, filed Jun. 10, 1999, which is in turn a continuation-in-part of commonly-owned copending U.S. application Ser. Nos. 09/096,332, filed Jun. 11, 1998, now U.S. Pat. No. 6,084,136 and 08/945,158, filed Oct. 21, 1997, now U.S. Pat. No. 6,084,137. U.S. application Ser. No. 09/096,332 is a continuation-in-part of U.S. application Ser. No. 08/945,158, filed Oct. 21, 1997, now U.S. Pat. No. 6,084,137, which in turn is a continuation-in-part of commonly-owned U.S. application Ser. Nos. 08/426,996 and 08/426,998 both filed Apr. 24, 1995 and both now abandoned. U.S. application Ser. No. 08/426,998 in turn is a continuation-in-part of commonly-owned U.S. application Ser. No. 08/398,837, filed Mar. 6, 1995 and now abandoned. U.S. application No. Ser. 08/945,158 is also a continuation-in-part of commonly-owned U.S. application Ser. No. 08/550,044, filed Oct. 30, 1995, now U.S. Pat. No. 5,723,690, which in turn is a continuation of commonly-owned U.S. application Ser. No. 08/426,997, filed Apr. 24, 1995, now U.S. Pat. No. 5,527,971.

OTHER COMMONLY-OWNED COPENDING APPLICATIONS

Reference is also made to other commonly-owned copending U.S. application Ser. Nos. 09/288,195, filed Apr. 8, 1999 and 09/407,314, filed Sep. 28, 1999.

TECHNICAL FIELD

This invention relates to novel, highly efficient processes for the preparation of tetrabromobisphenol-A.

BACKGROUND

Tetrabromobisphenol-A is one of the most widely used brominated flame retardants in the world. It is used extensively to provide flame retardancy for styrenic thermoplastics and for some thermoset resins.

Processes used for producing tetrabromobisphenol-A generally fall into three categories. The first category includes processes in which substantial amounts of methyl bromide are co-produced along with the tetrabromobisphenol-A. Generally, up to 40–50 pounds of methyl bromide can be expected per 100 pounds of tetrabromobisphenol-A produced. In most cases, the processes within this first category feature reacting bisphenol-A and bromine in methanol. The ring-bromination of the bisphenol-A is a substitution reaction which generates one mole of HBr per ring-bromination site. Thus, for the production of tetrabromobisphenol-A, four moles of HBr are generated per mole oftetrabromobisphenol-A produced. The HBr in turn reacts with the methanol solvent to produce the methyl bromide co-product. After the bisphenol-A and bromine feed are finished, the reactor contents are cooked for one to two hours to complete the reaction. At the end of the reaction, water is added to the reactor contents to precipitate out the desired tetrabromobisphenol-A product.

The second category of processes features the production of tetrabromobisphenol-A without the co-production of substantial amounts of methyl bromide and without the use of oxidants to convert the HBr to $Br_2$. See for example U.S. Pat. No. 4,990,321; U.S. Pat. No. 5,008,469; U.S. Pat. No. 5,059,726; and U.S. Pat. No. 5,138,103. Generally, these processes brominate the bisphenol-A at a low temperature, e.g., 0 to 20° C., in the presence of a methanol solvent and a specified amount of water. The water and low temperature attenuate the production of methyl bromide by slowing the reaction between methanol and HBr. The amount of water used, however, is not so large as to cause precipitation of the tetrabromobisphenol-A from the reaction mass during the bromination reaction. Additional water for that purpose is added at the end of the reaction. This type of process typically uses a fairly long aging or cook period after the reactants have all been fed, and requires additional process time for the final precipitation of tetrabromobisphenol-A via the last water addition.

In the third category are those processes which feature the bromination of bisphenol-A with bromine in the presence of a solvent and, optionally, an oxidant, e.g., $H_2O_2$, $Cl_2$, etc. See for example U.S. Pat. No. 3,929,907; U.S. Pat. No. 4,180,684; U.S. Pat. No. 5,068,463 and Japanese 77/034620 B4 77/09/05. The solvent is generally a water-immiscible halogenated organic compound. Water is used in the reaction mass to provide a two-phase system. As the bisphenol-A is brominated, the tetrabromobisphenol-A is formed in the solvent. The co-produced HBr is present in the water. When used, the oxidant oxidizes the HBr to $Br_2$, which in turn is then available to brominate more bisphenol-A and its under-brominated species. By oxidizing the HBr to $Br_2$, only about two moles of $Br_2$ feed are needed per mole of bisphenol-A fed to the reactor. To recover the tetrabromobisphenol-A from the solvent, the solution is cooled until tetrabromobisphenol-A precipitation occurs. The cooling of the solution to recover tetrabromobisphenol-A entails additional expense and process time.

Process technology for producing tetrabromobisphenol-A is described in commonly-owned U.S. Pat. Nos. 5,527,971, 5,723,690, 5,847,232, 6,002,050, 6,084,136, and 6,084,137, and in commonly-owned U.S. patent application Ser. Nos. 09/288,195, filed Apr. 8, 1999, 09/329,374, filed Jun. 10, 1999, 09/407,314, filed Sep. 28,1999, and 09/416,855, filed Oct. 12, 1999.

THE INVENTION

This invention makes it possible to produce tetrabromobisphenol-A on a continuous basis wherein the use of bromine feeds can be eliminated or at least greatly minimized, wherein steady state operation can be rapidly achieved after plant startup, and wherein such steady state operation can be maintained with minimal process controls. At the same time these objectives can be achieved without sacrifice of other advantageous features of the commonly-owned technology, such as forming during the bromination precipitated tetrabromobisphenol-A that is highly pure, of minimal, if any, color, readily recoverable, and formed in high yield based on the bisphenol-A fed to the reaction.

The processes of this invention thus feature the efficient production of high-quality, low-color tetrabromobisphenol-A in high yields under operating conditions that avoid localized concentrations of bromine in the reaction mass and that make possible the maintenance of a bromination reaction mass of substantially uniform composition throughout substantially the entire bromination reaction. Although the processes of this invention can be run in a semi-continuous mode, the greatest benefits are achievable when the operation is conducted in a continuous mode.

When run in a semi-continuous mode, process efficiency is enhanced due to relatively short reaction times and the absence of a need for a time-consuming one hour plus post-reaction cook period or a post-reaction tetrabromobisphenol-A precipitation step. The use of a continuous process for the production of tetrabromobisphenol-A is a rarity in itself and is made possible by the short reaction and tetrabromobisphenol-A precipitation times which are features of processes of this invention. In the continuous mode, reactor size can be substantially reduced without a loss in product output.

In addition to the above reaction efficiencies, the processes of this invention are capable of producing high yields of tetrabromobisphenol-A in a methanol- or ethanol-based solvent without the substantial concomitant production of methyl bromide or ethyl bromide, e.g., as little as 0.2 to 1.0 lbs (ca. 0.09 to ca. 0.45 kg) of methyl bromide or ethyl bromide per 100 lbs (ca. 45.4 kg) of tetrabromobisphenol-A product. Even further, it is possible to obtain high yields of almost pure white tetrabromobisphenol-A even though excess unreacted bromine is present in the reaction mass during substantially all of the time steady state bromination conditions have been established.

Pursuant to this invention there is provided in one of its embodiments a process of producing tetrabromobisphenol-A, which process comprises:

a) concurrently feeding to a reactor (i) a first continuous feed stream composed of bisphenol-A and/or underbrominated bisphenol-A and a water-miscible organic solvent, (ii) a second continuous feed composed of gaseous hydrogen bromide and/or aqueous hydrobromic acid, and (iii) a third continuous feed composed of aqueous hydrogen peroxide, at relative rates that maintain in the reactor during at least a substantial portion of such concurrent feeding, a reaction mass having a liquid phase containing from above about 15 to about 85 wt % water, and preferably in the range of about 30 to about 85 wt % water, the wt % being based upon the amount of water and water-miscible organic solvent in the liquid phase of the reaction mass;

b) during at least a substantial portion of the concurrent feeding in a), maintaining the temperature of the reaction mass within the range of about 30 to about 100° C.;

c) during at least a substantial portion of the concurrent feeding in a), providing the continuous feeds at relative rates (i) that maintain in the liquid phase of the reaction mass an amount of unreacted bromine that is in excess over the stoichiometric amount theoretically required to convert the bisphenol-A and/or underbrominated bisphenol-A to tetrabromobisphenol-A, and to continuously form during substantially all of the time the feeding in a) is occuring, a precipitate comprised mainly of tetrabromobisphenol-A, and (ii) that result in a yield of precipitated tetrabromobisphenol-A during substantially all of the time the feeding in a) is occurring of at least about 90% based on the amount of the bisphenol-A or underbrominated bisphenol-A or combination thereof fed up to that point in time; and d) during at least a substantial portion of the concurrent feeding in a), withdrawing from the reactor a mixture of precipitated tetrabromobisphenol-A and a potion of the liquid phase of the reaction mass, such that the volume of the contents of the reactor remains substantially constant during at least a substantial portion of the concurrent feeding in a).

Reference anywhere in this document to bromine in the liquid phase of the reaction mass should be understood to mean unreacted bromine, as distinguished from total bromine which would include both unreacted and reacted bromine. And as any chemist would readily understand, reference to unreacted bromine in the liquid phase does not include the bromine content of HBr present in the liquid phase.

When conducting the processes of this invention it is preferred that no elemental bromine be fed into the reactor. In other words, except for a possible charge of elemental bromine as part of a heel to initiate the continuous process, it is preferred to rely entirely on the hydrogen bromide and/or the hydrobromic acid fed to the reactor plus the HBr co-product of the bromination that remains in the liquid phase of the reaction mass as the source of the bromine for the bromination, the bromine thus being totally formed in situ. However, it is possible pursuant to this invention to continuously feed elemental bromine in an amount constituting a small portion of the total bromine requirements for the process. In such case the process is conducted using the concurrent feeds described above while also concurrently feeding elemental bromine into the reactor (most preferably widely distributed at locations below the surface of the liquid phase of the reaction mass), the bromine feed being at a substantially constant rate and in quantity such that the mole ratio of $Br_2$ to HBr being fed does not exceed about 0.5:1.

In another embodiment of this invention there is provided a process for the production of tetrabromobisphenol-A, which process comprises:

a) providing a steady-state liquid phase reaction system to which at least a first feed of bisphenol-A and/or underbrominated bisphenol-A and a water-miscible organic solvent, a second feed of gaseous hydrogen bromide and/or aqueous hydrobromic acid, and a third feed of aqueous hydrogen peroxide, are being continuously fed and in which there is being continuously formed a tetrabromobisphenol-A precipitate by the bromination of bisphenol-A and/or underbrominated bisphenol-A with an excess of bromine over the stoichiometric amount theoretically required to produce tetrabromobisphenol-A, and in which 1) all of the bromine in the steady-state liquid phase reaction system (i.e., excluding the startup of the process where bromine may be used if desired) is formed in situ by reaction between the HBr and the $H_2O_2$, or 2) a portion, but no more than 50 mole percent, and preferably no more than 10 mole percent, of the bromine is continuously fed into the system as bromine, with the balance of the bromine being formed in situ by reaction between the HBr and the $H_2O_2$, such that tetrabromobisphenol-A is being formed continuously in a yield of at least about 90% based on the amount of the bisphenol-A and/or underbrominated bisphenol-A already fed;

b) agitating and/or refluxing the reaction system so as maintain a substantially uniform slurry within the reaction system; and c) continuously separating from the reaction mass, an amount of the substantially uniform slurry to continuously maintain the reaction system at substantially constant volume.

In both of the above embodiments it is preferred to employ aqueous hydrobromic acid rather than gaseous hydrogen bromide as the external source of bromine for the process. Among the reasons for this is that the aqueous hydrobromic acid contributes to maintenance of the water content of the reaction mass which is a necessary feature of the process. Also, close control of liquid feeds such as aqueous hydrobromic acid is generally more readily achieved than with gaseous feeds such as hydrogen bromide. Moreover, the feed of aqueous hydrobromic acid to a water-containing reaction mass is less likely to result in localized excess concentrations of HBr within the reaction mass.

A further embodiment of this invention is a bromination process in which tetrabromobisphenol-A is produced with little or no bromine being fed to the bromination reaction mass, the process being characterized by maintaining at least three concurrent separate continuous feeds to a reaction mass having a liquid phase composed of a water-miscible organic solvent and water, these three feeds being composed of (1) bisphenol-A and/or underbrominated bisphenol-A and the water-miscible organic solvent, (2) aqueous hydrobromic acid, and (3) aqueous hydrogen peroxide. These feeds are being proportioned and the reaction mass is being maintained at a temperature such that under steady-state reaction conditions:

a) bromine and water are being continuously formed in situ by oxidation of HBr by $H_2O_2$, b) tetrabromobisphenol-A is being continuously formed via bromination as a solids phase in an overall yield of at least about 90% based on the amount of the bisphenol-A and/or underbrominated bisphenol-A already fed, c) hydrogen bromide is being continuously formed in situ as a co-product of the bromination in b), d) an excess amount of unreacted bromine is continuously present in the liquid phase of the reaction mass, and e) the amounts of water being fed and being generated in situ continuously maintain the water content in the liquid phase of the reaction mass high enough to cause the tetrabromobisphenol-A to continuously precipitate from the liquid phase substantially at the same time tetrabromobisphenol-A is being continuously formed.

An optional feature of this embodiment involves providing a portion, but no more than 50 mole percent, and preferably no more than 10 mole percent, of the bromine in the liquid phase of the reaction mass by continuously feeding this portion of bromine into the reaction mass as bromine, with the balance of the bromine being formed in situ by reaction between the HBr and $H_2O_2$ being fed. Another feature of this embodiment is to mechanically agitate and/or reflux the reaction mass to maintain substantial uniformity in the reaction mass. Continuously separating a portion of the substantially uniform reaction mass from the remainder of the reaction mass, preferably in an amount to continuously maintain the reaction mass at substantially constant volume, are additional features of this embodiment.

Important features of this invention are that not only is the bromination reaction very rapid especially under preferred temperature conditions used (from about 50 to about 100° C.), but during all or substantially all of the time the reactants ($Br_2$ and bisphenol-A and/or underbrominated bisphenol-A) are coming in contact with each other in the liquid phase of the reaction mass under the specified conditions, a precipitate is being formed that (i) typically contains at least about 90 wt %, and preferably at least about 95 wt % of tetrabromobisphenol-A, and (ii) typically is formed in a yield of at least about 90% based on the amount of bisphenol-A and/or underbrominated bisphenol-A fed to the reaction mass. Moreover, even though the liquid phase of the reaction mass contains at substantially all times during the concurrent feeds an amount of unreacted bromine— perhaps as much as 20,000 ppm of unreacted bromine, but preferably no more than about 10,000 ppm—the tetrabromobisphenol-A being produced is of low color (e.g. it will have an APHA color of 100 or less, and usually 50 or less, the APHA color being determinable by dissolving 80 grams of the tetrabromobisphenol-A product in 100 mL of acetone).

Rapid, high yield formation of the tetrabromobisphenol-A product as a precipitate facilitates the recovery of the product, as this can be effected by any of a variety of physical separation procedures such as draining, decantation, centrifugation, and/or filtration. More particularly, the precipitate enriched in the desired product is removed from the reaction mass continuously or substantially continuously, along with a portion of the reaction mass, whereby the volumes of feeds to, and material removed from, the reactor are kept constant or substantially constant at all times. The presence in the liquid phase of the reaction mass of excess unreacted bromine over and above that required to convert the bisphenol-A and/or underbrominated bisphenol-A to tetrabromobisphenol-A ensures that this desired product is formed in high yield without significant contamination by underbrominated bisphenol-A such as tribromobisphenol-A. And since all, or substantially all of the bromine is produced in situ by rapid oxidation of HBr by hydrogen peroxide with both such reactants in the liquid phase, it is possible to engender bromine formation substantially uniformly throughout substantially the entire liquid phase of the reaction mass, e.g., by use of agitation or by refluxing the liquid phase, or both. This in turn eliminates localized concentrations of bromine, such as can occur when rapidly feeding large amounts of elemental bromine to the reaction mass. Use of such agitation or refluxing also ensures that the liquid feed of bisphenol-A and/or underbrominated bisphenol-A plus organic solvent entering the liquid phase of the reaction mass is also substantially uniformly distributed throughout the reaction mass. Consequently, the tetrabromobisphenol-A particles are formed substantially uniformly throughout the reaction mass, and therefore the tetrabromobisphenol-A precipitate plus the portion of the reaction mass being continuously removed from the reactor remains substantially uniform in composition during substantially the entire time the concurrent feeds are taking place. Thus once steady state conditions have been achieved, continuous operation of the process requires a minimum of process controls.

The HBr fed to and generated in situ as the by-product of the bromination reaction serves at least a dual role in the process. First, the HBr in the water-containing reaction mass tends to keep the tetrabromobisphenol-A from developing color as it the tetrabromobisphenol-A is being formed as a precipitate in the reaction mass. Secondly, the HBr serves as the sole source, or at least a major source, of the bromine used in the bromination reaction. In addition, the use of aqueous hydrobromic acid as one of the concurrent feeds avoids the difficulties that can arise when feeding a gaseous reactant (e.g., incorrect or imprecise metering into the reaction mass). Moreover, use of an aqueous hydrobromic acid feed serves as a way of feeding a significant portion of the water to maintain the desired composition of the liquid phase of the reaction mass during the concurrent feeds by contributing to the replenishment of the water concurrently being withdrawn from reactor as part of the reaction mass that is being withdrawn from the reactor along with tetrabromobisphenol-A precipitate.

The fact that a substantial quantity of water is continuously maintained in the liquid phase of the reaction mass contributes to the high efficiency of the process. In the first place, the water in the liquid phase causes the tetrabromobisphenol-A product to precipitate from the liquid phase essentially as soon as the tetrabromobisphenol-A is formed. Such continuous rapid precipitation occurs because the quantity of water present in the liquid phase provides a liquid medium in which the tetrabromobisphenol-A is quite insoluble. Secondly, the water in the liquid phase of the reaction mass contributes significantly to the retention in the liquid phase of a large proportion of the HBr as it is being co-produced from the continuous bromination. That is to say, hydrobromic acid is formed in situ by interaction of HBr co-product and water in the reaction mass. Thus losses of HBr to the headspace in the reactor, if any, are typically very small. This in turn ensures that most, if not all, of the HBr retained in the liquid phase will be converted in situ to bromine via oxidation by the hydrogen peroxide being charged to the reactor. Thus there is at least a duality of function for the water in the liquid phase of the reaction mass. As noted hereinafter, it is believed that still another function served by the water is that of controlling of the amount of alkyl bromide co-product formed when the water-miscible solvent used is an alcohol.

Since excess bromine is to be present in the liquid phase in the reactor, the source of the bromine thus consists of (i) bromine generated in situ by oxidation of HBr or (ii) a combination of a relatively small proportion of bromine fed to the reactor in liquid and/or gaseous form plus a relatively large proportion of bromine generated in situ by oxidation of HBr. The HBr that is oxidized to bromine is typically a combination of HBr co-product from the bromination plus HBr fed to the reactor. While in theory it may be possible to use only HBr fed to the reactor as the source of HBr subjected to the in situ oxidation, this would require segregating the coproduct HBr from the HBr fed to the reactor.

In the practice of this invention the amount of unreacted bromine maintained in the liquid phase of the reaction mass typically will not exceed about 3.5 wt % (ca. 35,000 ppm). Preferably the amount of bromine in the liquid phase of the reaction mass is kept in the range of about 50 to about 20,000, and more preferably in the range of about 50 to about 10,000 parts per million (ppm) during substantially the entire bromination period. As can be seen from the foregoing, and as is conventional, all parts referred to in any portion of this document are by weight unless otherwise expressly indicated.

In conducting the concurrent feeds referred to above, once steady-state reaction conditions have been established, it is most preferred to maintain all feeds on a uniform continuous basis to thereby maintain a steady-state liquid phase reaction system. However, minor fluctuations in the concentrations of the respective feeds or temporary short interruptions in one or more of the feeds can be tolerated as long as such fluctuations or interruptions do not cause an irreparable loss of the steady-state reaction conditions.

This invention in its various forms referred to above thus provides in essence a process wherein tetrabromobisphenol-A product is produced by providing a liquid phase reaction system in which there is directly formed a tetrabromobisphenol-A precipitate by the bromination of bisphenol-A and/or underbrominated bisphenol-A. The bromination involves use of an excess of bromine over the stoichiometric amount theoretically required to produce tetrabromobisphenol-A. All, or at least the vast majority of the bromine in the reaction system is generated in situ from HBr, at least part of which is continuously fed as HBr, preferably as aqueous hydrobromic acid. Typically HBr co-product is also oxidized in situ to bromine. The bromination is thus conducted in the presence of an amount of HBr that is high enough to protect the tetrabromobisphenol-A being produced from excessive color development. Moreover, the bromination is conducted at such rate that (i) there is insufficient opportunity for significant precipitation of the intermediate, tribromobisphenol-A, to occur, and (ii) while the bisphenol-A and/or underbrominated bisphenol-A is/are being brought into contact with unreacted bromine in the liquid phase of the reaction mass, tetrabromobisphenol-A is being produced substantially continuously. Typically the yield of the tetrabromobisphenol-A as it is being produced substantially continuously is at least about 90%, and preferably at least about 95% based on the amount of the bisphenol-A and/or underbrominated bisphenol-A already fed. In addition the tetrabromobisphenol-A produced typically has an APHA color of less than about 100, preferably 50 or less, the APHA color being determinable by dissolving 80 grams of the tetrabromobisphenol-A product in 100 mL of acetone.

Other embodiments and features of the invention will become still further apparent from the ensuing description and appended claims. The ensuing description refers primarily to the conduct of the processes of this invention once steady-state operating conditions have been achieved. Conditions for process initiation or startup which may differ to some extent from steady-state conditions are identified in the text.

As noted above, the organic reactant used in the practice of this invention is bisphenol-A and/or underbrominated bisphenol-A. The term "underbrominated bisphenol-A" refers to one or more brominated bisphenol-A compounds in which less than the four ortho-positions relative to the hydroxyl groups are substituted by a bromine atom. Typically, the major underbrominated bisphenol-A species is the tribrominated species (3,5-dibromo-4-hydroxyphenyl) (3-bromo-4-hydroxyphenyl)dimethylmethane), but one or more other underbrominated species may be present such as either or both of the dibromo species, 3,5-dibromo-4-hydroxyphenyl)(4-hydroxyphenyl)dimethylmethane and bis (3-bromo-4-hydroxy-phenyl)dimethylmethane, and/or the monobromo species (3-bromo-4-hydroxyphenyl)(4-hydroxyphenyl)dimethylmethane. Therefore the organic reactant fed to the reactor can be bisphenol-A only, any one of these underbrominated bisphenols only, any combination of any two or more of these underbrominated bisphenol-A species only, or any combination of bisphenol-A and any one or more of these underbrominated bisphenol-A species. The preferred organic reactant fed to the reactor is bisphenol-A itself. Of course during the bromination, the bisphenol-A is transformed into various underbrominated bisphenol-A species until it becomes tetrabromobisphenol-A. The same holds true for the various underbrominated bisphenol-A species which during bromination finally become tetrabromobisphenol-A. Therefore the term "bisphenol-A and/or underbrominated bisphenol-A" in this document refers to the identity of the compound as it exists prior to being fed into the bromination reaction mass.

The water-miscible organic solvent can be defined functionally as a material which is capable of solvating $Br_2$, bisphenol-A, monobromobisphenol-A, dibromobisphenol-A and tribromobisphenol-A under reaction conditions. Further, the organic solvent should be substantially inert with regard to $Br_2$, $H_3OBr$ and the ring-bromination of the bisphenol-A to tetrabromobisphenol-A and not contribute to the production of troublesome amounts of color bodies, ionic bromides and/or hydrolyzable bromides. Hydrolyzable bromides can include 1-bromo-2-alkoxy-2-(3',5'-dibromo-4'-hydroxyphenyl)propane, 1,1-dibromo-2-alkoxy-2-(3',5'-dibromo-4'-hydroxyphenyl)propane, 1,3-dibromo-2-alkoxy-2-(3',5'-dibromo-4'-hydroxy-phenyl)propane, and 1,1,3-tribromo-2-alkoxy-2-(3',5'-dibromo-4'-hydroxyphenyl) propane. The solvent, when taken in combination with the water and reaction conditions of the processes of this invention, can have some small ability to solvate tetrabromobisphenol-A, but for the sake of reaction yield, the solvating power should be low, say no more than about 20 wt % and preferably no more than about 5 wt % solvated tetrabromobisphenol-A in the liquid phase of the reaction mass.

Exemplary of the preferred water-miscible organic solvents are water-miscible alcohols (eg., methyl alcohol, ethyl alcohol, n-propyl alcohol, isopropyl alcohol, tert-butyl alcohol), water-miscible carboxylic acids, (e.g., acetic acid, propionic acid), and water-miscible nitriles, (e.g., acetonitrile). Some water-miscible ethers may also be suitable provided they are not cleaved by the acidic nature of the reaction mass. Mixtures of two or more suitable organic solvents can be employed. The more preferred solvents are the alcohols having up to 4 carbon atoms. Even more preferred are ethanol and methanol as they are relatively inexpensive and are easily recovered by simple distillation techniques for recycle. Ethanol is most preferred. It is to be understood and appreciated that the organic solvent need not be soluble in water in all proportions at, say, 20° C. Although such total miscibility is preferable, the organic solvent should at least have sufficient solubility in water in the proportions and at the bromination temperature(s) being employed to form a clear one-phase homogeneous liquid reaction medium from which tetrabromobisphenol-A product will precipitate during the bromination.

The amount of water-miscible organic solvent used is best related to the amount of bisphenol-A fed and can be conveniently expressed as the weight ratio of the organic solvent to bisphenol-A. Typically, the ratio is within the range of from about 1:1 to about 10:1, preferably within the range of from about 2:1 to about 10:1, and most preferably the ratio is within the range of from about 3:1 to about 5:1. More or less organic solvent can be used, provided that the solvent function mentioned above is accomplished.

The water-miscible organic solvent is preferably fed to the reactor as a constituent of a solution or slurry of bisphenol-A and/or underbrominated bisphenol-A. However, if desired, only a portion of the organic solvent can be fed as part of the bisphenol-A and/or underbrominated bisphenol-A solution or slurry, with the remaining portion, generally a smaller portion, being fed as a separate stream. The temperature of the feed stream of the solution or slurry of bisphenol-A and/or underbrominated bisphenol-A in the water-miscible organic solvent should be such as to result in efficient operation, and the temperature selected for the feed should take into consideration the desired reaction mass temperature to be used. Thus the feed stream can be fed at room temperature, or at a temperature above or below room temperature, and therefore, the temperature selected for the feed stream can be used as a way of assisting in the regulation of the reaction mass temperature. However, the temperature of the feed stream should not be above the boiling temperature or below the freezing temperature of the water-miscible organic solvent, or otherwise result in interfering with the continuous free flow of the feed stream into the reactor. Also, the temperature of this feed stream should not detrimentally cool or heat the reaction mass. The foregoing comments with regard to temperature also apply to that portion of the water-miscible organic solvent that may be separately fed into the reactor, if any such separate feed is to be employed.

When the water-miscible organic solvent used is ethanol, it is preferred to produce no more than about 4.54 kg (10 lbs) of ethyl bromide per 45.4 kg (100 lbs) of tetrabromobisphenol-A precipitate produced.

HBr, preferably as aqueous hydrobromic acid, constitutes another of the concurrent continuous feeds to the reactor. Aqueous hydrobromic acid being fed will typically be a solution containing in the range of about 10 to about 50 wt % of HBr, and preferably will contain in the range of about 20 to about 50 wt % of HBr. Most preferably the HBr content is in the range of about 40 to about 48 wt % of HBr. This feed stream can be introduced while at room temperature, or it can be fed at a suitable temperature above or below room temperature to assist in maintaining the desired temperature reaction mass during steady-state operating conditions.

Another concurrent feed to the reactor is aqueous hydrogen peroxide. Although it is possible pursuant to this invention to use other oxidant materials, e.g., small proportions of chlorine, to generate bromine in situ, aqueous hydrogen peroxide is by far the most preferred oxidant. The function of the oxidant is to oxidize HBr to $Br_2$ in the reaction mass and under the process conditions of this invention, and it must do so without materially interfering with the bromination reaction. Safety considerations make it desirable to feed the $H_2O_2$ to the reaction mass as an aqueous solution containing no more than about 90 wt % $H_2O_2$. Preferred are aqueous solutions containing from about 20 to about 80 wt % $H_2O_2$. A more preferred solution is one containing from about 30 to about 70 wt % $H_2O_2$, with a solution containing about 30 to about 50 wt % $H_2O_2$, being especially preferred. The use of a continuous aqueous feed to the reactor of hydrogen peroxide is also advantageous in that the feed assists in maintaining the appropriate water level in the reaction mass by compensating in part for the water that is being removed as part of the reaction mass concurrently being removed from the reactor. Usually this feed stream will be fed while it is at about room temperature, although some departure from room temperature can be resorted to as long as the temperature does not cause decomposition of the solution or otherwise adversely interfere with the bromination reaction conditions in the reaction mass.

If bromine is to be fed during reaction startup or as one of the concurrent feeds to the reactor when operating under steady state reaction conditions, use can be made of commercially available $Br_2$ of suitable purity. Should the $Br_2$ contain undesirable impurities, it can be treated by conventional purification techniques, e.g., distillation, $H_2SO_4$ treatment, etc., which are well known to those skilled in the art.

The $Br_2$, if and when fed to the reactor, can be fed as a liquid or as a gas. It is preferred that the feed be gaseous. Whether the $Br_2$ is liquid or gaseous, it is preferred that the feed entry point be sub-surface of the reaction mass. This is conveniently accomplished by use of one or more dip tubes. Preferably the ports of entry for the bromine are widely disseminated in the reaction mass so that the feed is spread out in a relatively uniform manner in the reaction mass, and so that the individual ports discharge small portions of the total feed thereby minimizing the possibility of localized high concentrations of bromine. If the feed is liquid, above-surface feed must contend with possible splattering, bromine loss due to evaporation, and inefficient mixing.

When bromine is fed to the reactor, the $Br_2$ is preferably at a temperature which promotes process efficiency in view of the desired reaction mass temperature. A suitable liquid $Br_2$ feed temperature is from about 10° C. to just below the boiling point of $Br_2$. If the $Br_2$ is to be fed as a gas, then the $Br_2$ stream temperature should be that which is conducive to such a feed. For example, such a feed temperature may be within the range of from about 60 to about 100° C. The solution feed temperature should be that which does not detrimentally cool or heat the reaction mass or which requires pressure operation so that the feed can be made in the liquid state.

The amount of water in the reaction mass should be within the range of from above about 15 to about 85 wt %, and typically is in the range of about 30 to about 85 wt % of water, based upon the total amount of water and water-miscible organic solvent in the liquid phase of the reaction mass. Preferably, the amount of water fed is that amount which is within the range of from about 30 to about 75 wt % water. Most highly preferred is the range of from about 30 to about 70 wt %. When the water-miscible organic solvent is methanol the preferred amount is from about 30 to about 55 wt %. With ethanol, the preferred amount of water is from about 40 wt % to about 65 wt %.

The water content of the reaction mass is an important aspect of this invention. Although this invention is not to be limited in any way by any particular theory, it is believed that the water content suppresses formation of methyl bromide or ethyl bromide and, at the same time, allows for production of high purity tetrabromobisphenol-A product. Normally, it might be expected that the water content would cause under-brominated species, e.g., tribromobisphenol-A, to precipitate along with the tetrabromobisphenol-A species, thereby yielding an impure product. However, the processes of this invention are in fact capable of producing product of desirable purity as well as product with little, if any, color.

It is possible to feed a portion of the water to the reactor as part of a solution or slurry which also contains bisphenol-A and/or underbrominated bisphenol-A and a water-miscible solvent. It is also possible to introduce part of the water into the reaction mass as a separate feed stream. This latter feed, if used, should be concurrent with the other feeds referred to above. Preferably, however, all of the water being introduced into the reactor, is fed by means of a feed of aqueous hydrobromic acid, and the concurrent feed of aqueous hydrogen peroxide solution, as this minimizes process controls. It should be kept in mind that two moles of water are formed in the reactor from each two moles of HBr that are oxidized to a mole of diatomic bromine by a mole of $H_2O_2$. No matter how the water is provided to the reaction mass, the chief requirement is that the proper amount of water be maintained in the reaction mass during substantially all of the reaction period so that precipitation of tetrabromobisphenol-A occurs as the bromination is proceeding.

The concurrent feeds to the reactor all contribute to the formation of the reaction mass in the reactor. These feeds will produce a reaction mass liquid phase (liquid portion) and, because of the formation of tetrabromobisphenol-A precipitate, ultimately, but rather quickly, a reaction mass solid phase (solid portion). Typically, the reaction mass is agitated and/or maintained under continuous reflux, such that the reaction mass is in the form of a substantially uniform slurry, with some small amount of non-uniformity due principally to the effect of gravity upon the reaction mass. A portion of the $Br_2$ in the reaction mass resulting from in situ oxidation of HBr and, if used, a limited feed of bromine, be it fed as a gas or as a liquid, will be consumed in the bromination reaction. Any non-consumed $Br_2$ feed will be found in the liquid phase and will be joined there by any non-consumed $Br_2$ produced by the oxidation of HBr present in the reaction mass.

The liquid phase of the reaction mass should continuously contain an excess of unreacted bromine relative to the amount of bisphenol-A and/or underbrominated bisphenol-A being continuously maintained in the liquid phase of the reaction mass. A stoichiometric amount of bromine is one molecule of diatomic bromine ($Br_2$) for each hydrogen atom present as a substituent in an ortho-position relative to the hydroxyl groups of bisphenol-A and/or underbrominated bisphenol-A present in the reaction mass. For example, if the feed were 1 mole of bisphenol-A and 1 mole of tribromobisphenol-A, there would be a total of 5 moles of hydrogen atoms in the ortho positions—i.e., 4 moles in the bisphenol-A and 1 mole in the tribromobisphenol-A. A stoichiometric amount of bromine in this particular case would therefore be equivalent to 5 moles of diatomic bromine, and pursuant to this invention an amount of bromine equivalent to more than 5 moles of bromine would be continuously maintained in the liquid phase of the reaction mass. Similarly, if the feed were, say, 1 mole of mono-orthobromobisphenol-A, there would be a total of 3 moles of hydrogen atoms in the ortho positions. A stoichiometric amount of bromine in this particular case would therefore be equivalent to 3 moles of diatomic bromine, and pursuant to this invention an amount of bromine equivalent to more than 3 moles of bromine would be continuously maintained in the liquid phase of the reaction mass. In accordance with this invention either (a) all of the bromine required for the bromination and to maintain the excess amount of unreacted bromine in the liquid phase of the reaction mass is generated in situ by oxidation of HBr, or (b) up to 50 mole %, and preferably up to 10 mole % of such bromine requirements is being fed as bromine itself with the balance being generated in situ by oxidation of HBr. Whichever such method used in providing these bromine requirements, the amount of unreacted bromine specified above should be continuously maintained in the liquid phase of the reaction mass.

As just pointed out, unreacted bromine in the liquid phase of the reaction mass should be present at all times during the concurrent feeds to the reactor. However, it is permissible, although not desirable, to make or to endure brief departures from this highly advantageous operating condition. In other words it is possible for the unreacted $Br_2$ content in the reaction mass to disappear for brief periods of time depending on the level of underbrominated species that can be tolerated in the tetrabromobisphenol-A reaction product and/or upon the extent of precipitation of the underbrominated species which is experienced. For best results, steady-state operating conditions should be reinstated as quickly as possible after such disappearance of bromine content from the reaction mass, so that more efficient operation is resumed and maintained. It is desirable when establishing the process parameters to be used in a given situation to observe the process and determine by empirical methods the sensitivity of the chosen reaction conditions to the brief absence of unreacted $Br_2$ in the reaction mass. Thus, for the purposes of this invention the feature of maintaining in the liquid phase of the reaction mass an amount of unreacted bromine that is in excess over the stoichiometric amount theoretically required to convert the bisphenol-A and/or underbrominated bisphenol-A to tetrabromobisphenol-A encompasses brief periods of time in which the unreacted bromine content can be nil, but which does not result in the formation of underbrominated species to an extent that results in an unacceptable tetrabromobisphenol-A product, say, one containing less that about 96 wt % tetrabromobisphenol-A.

In producing bromine from HBr, the stoichiometry involves two moles of HBr and one mole of hydrogen peroxide to form one mole of diatomic bromine ($Br_2$). Two moles of water are co-produced. Among the advantages of this invention is that both the bromination and the in situ HBr oxidation reactions are rapid, especially when operating with the reaction mass temperature within the range of about 30 to about 100° C., and especially in the range of about 60 to about 100° C.

Another advantage of the processes of this invention is that HBr is a relatively inexpensive bromine source. Gaseous HBr is often produced in substantial quantities in various industrial chemical processes, and it is relatively easy to convert such HBr to hydrobromic acid by dissolving the HBr in water. Moreover, it is not necessary to closely control the amount of aqueous hydrobromic acid being fed to the reactor as long as the desired water content of the liquid phase of the reaction mass is not exceeded. The amount of bromine being generated in situ from the HBr present in the liquid phase (fed HBr and co-product HBr) of the reaction mass can be regulated and controlled by regulating the amount of hydrogen peroxide being fed to the reaction mass. The excess unreacted HBr can thus be recovered from the liquid phase of the reaction mass being continuously withdrawn from the reactor and used as recycle to the process.

While on the subject of stoichiometry, it will be recalled that for every atom of bromine introduced into the bisphenol-A or underbrominated bisphenol-A molecule during the bromination, one molecule of HBr is produced. In other words, for every mole of diatomic bromine ($Br_2$) that reacts with the bisphenol-A or underbrominated bisphenol-A, one mole of HBr coproduct is produced. Therefore this HBr that is automatically generated in situ should be taken into consideration in designing the feeds and feed rates to be used in the reaction in order to maintain the requisite amount of HBr in the liquid phase of the reaction mixture. Although most of such coproduct HBr will usually remain in the liquid phase, some HBr may escape into the headspace of the reactor. The amount of such vaporized HBr will depend on such factors as the rate at which the bromination reaction is proceeding, the amount of water present in the liquid phase, the rate of agitation, if any, being used, and the pressure conditions in the reactor. Therefore, in any given situation where the conditions for producing and maintaining the particular amount of HBr desired in the liquid phase of the reaction mass during the time the reactants are being brought into contact with each other so that bromination is taking place, are not already known, it is desirable to perform a few preliminary pilot experiments in which the calculated feeds are adjusted to achieve the optimal conditions for achieving the desired amount of HBr in the liquid phase of the reaction mass.

Thus, quantifying for a selected set of operating conditions the preferred target amount of unreacted $Br_2$ to be present in the reaction mass liquid phase is best handled by a trial and error technique. A trial process is first defined by choosing an unreacted $Br_2$ target level and the other process parameters. The produced tetrabromobisphenol-A product from the process is analyzed for its tri- and tetrabromobisphenol-A content. If the tribromobisphenol-A level is too high, another trial process is constructed with a higher target unreacted $Br_2$ level. The procedure is repeated until the desired product is obtained. It is to be noted that some benefit towards reducing the tribromobisphenol-A content in the precipitate can also be obtained by using a higher reaction temperature. As the chosen unreacted $Br_2$ content gets higher, care should be taken that the unreacted $Br_2$ content will not be so high that it results in the production of tribromophenol and other by-products which are not desirable from a commercial standpoint.

Quantitative determination of the amounts of unreacted bromine and HBr in the liquid phase of the reaction mass is best conducted by sampling the reaction mass at intervals during the bromination, removing solids from the samples and analyzing the samples for their contents of bromine and HBr. While the particular methods of analysis used are not critical as long as they are of suitable accuracy and precision, the following overall analytical procedures are recommended:

Determination of Unreacted Bromine:

A weighed aliquot of the clear reaction mass mother liquor (about 1 mL sample) is dispersed into 100 mL of 2% potassium iodide solution. Starch is added as an indictor. Blue color indicates the presence of bromine. The stirred mixture is titrated against 0.01 N sodium thiosulfate solution to a clear end point. Unreacted bromine is calculated as follows:

$$\text{Wt \% Bromine} = \frac{\text{mL of sodium thiosulfate} \times \text{Normality of sodium thiosulfate} \times 8}{\text{Sample weight in grams}}$$

Determination of Hydrogen Bromide:

A weighed aliquot (about 1 mL sample) of the clear reaction mass mother liquor is mixed with 50 mL of deionized water. About 10 drops of 0. 1% aqueous bromocresol green indicator solution is added and titrated with 0.5N NaOH solution to a blue end point. Amount of hydrogen bromide is calculated as follows:

$$\text{Wt \% HBr} = \frac{\text{mL of NaOH} \times \text{Normality of NaOH} \times 8.091}{\text{Sample weight in grams}}$$

Once steady-state reaction conditions are in place, continual monitoring of unreacted bromine content in the liquid phase is unnecessary,. From then on only periodical monitoring is necessary to ensure that the process is functioning pursuant to this invention. Moreover, once the steady-state conditions are in place, the frequency of HBr analyses can be reduced to periodical checking to be sure that some upset such as line pluggage or etc. has not occurred.

It is possible to estimate the unreacted $Br_2$ content of the liquid phase of the reaction mass by the use of colorimetric techniques. A technique which can be used comprises the formation of an acidic (HBr) water and methanol or ethanol solution. From this solution, several standard samples are prepared, to each of which is added a different and measured amount of $Br_2$. The colors of these sample solutions are then compared colorimetrically with the color of the liquid of phase of the reaction mass. A color match is indicative of the amount of $Br_2$ in the liquid phase. Colorimetric determination for unreacted $Br_2$ is quite suitable as unreacted $Br_2$ colors the sample solutions and the reaction mass in accordance with its concentration. Low concentrations give a pale yellow color; intermediate concentrations give a strong yellow color; high concentrations give an orange color; and the highest concentrations give a dark red color. Unreacted $Br_2$ concentrations up to about 10,000 ppm, based upon the reaction mass liquid portion, are preferred, although smaller excesses above stoichiometric can be used. As noted above, an excess of as high as about 35,000 ppm of unreacted bromine in the liquid phase can be tolerated, although typically the excess will not be above about 20,000 ppm, with the a more preferred amount of unreacted bromine being within the range of from about 50 to about 10,000 ppm.

The unreacted $Br_2$ concentrations are maintained in the reaction mass so long as bisphenol-A and underbrominated species are likewise present. As can be appreciated, the unreacted $Br_2$ content diminishes as the $Br_2$ reacts, thus, the HBr and hydrogen peroxide feeds, and if used, a $Br_2$ feed, act to replenish the $Br_2$ in the reaction mass. Using the above-described colorimetric technique, the unreacted $Br_2$ content of the reaction mass can be monitored during the process and the unreacted $Br_2$ content within the chosen target range can be maintained, if necessary, by appropriate adjustment of the feed rates to achieve and maintain steady-state operation. Since there will be tetrabromobisphenol-A precipitate in the reaction mass, colorimetric monitoring may require that a small stream be taken from the reactor and filtered to remove the solids before being submitted to a colorimetric technique. It may also be possible to read the intensity of the reaction mass color without filtration by the use of reflectance techniques which measure the intensity of the light reflected off of the reaction mass. In all of the colorimetric cases, the color of the liquid phase of the reaction mass can be used as a way of estimating bromine concentration.

Upon termination of a continuous operation, e.g., for scheduled maintenance, the excess $Br_2$ present in the final portion of the reaction mass after completion of the process can be removed by treating the reaction mass with a reducing agent such as sodium sulfite or hydrazine.

Another important consideration in practicing the processes of this invention is the reaction mass temperature for the bromination. It is desirable to use a relatively high temperature so that the bromination of the bisphenol-A to tetrabromobisphenol-A will be sufficiently fast to reduce the extent of tribromobisphenol-A precipitate formation. However, there is a practical limit as to how high the temperature can be. For example, temperatures which would cause the production of unacceptable levels of unwanted by-products or the degradation of the tetrabromobisphenol-A product should not be used.

It is unusual to operate a tetrabromobisphenol-A process at relatively high temperatures, especially when production of a co-product such as methyl bromide or ethyl bromide is to be minimized. Also, use of relatively high temperatures might be expected to complicate the process by increasing the solubility of the tetrabromobisphenol-A in the solvent solution and possibly necessitate a final cooling of, or addition of water to, the reaction mass to effect the desired high yield precipitation of tetrabromobisphenol-A. The processes of this invention, however, can be operated without excessive coproduction of methyl bromide or ethyl bromide, and there is no requirement for a cooling step to obtain sufficient tetrabromobisphenol-A precipitation.

Operation at relatively high temperatures can contribute to additional process economy and product purity enhancement. Process economy, in part, can be realized because even at higher reaction mass temperatures, cooling tower water can be used to cool the reactor instead of using refrigeration which is required by processes that are operated at low temperatures.

Typically temperatures are within the range of from about 30 to about 100° C., and preferably are in the range of about 50 to about 100° C. More highly preferred temperatures are within the range of from about 50 to about 80° C. Essentially constant and uniform reaction mass temperatures within these ranges are typically maintained when operating a process of this invention. However, programmed fluctuations in temperature within these ranges may be utilized in continuous operations, if desired. The most highly preferred temperatures are within the range of from about 50 to about 70° C. Temperatures below 30° C. can be used, but the organic solvent to bisphenol-A and/or underbrominated bisphenol-A weight ratio may well need to be high, say from 8:1 to 15:1. For these ratios, temperatures of 30 to 50° C. may be suitable.

The bromination of bisphenol-A and/or underbrominated bisphenol-A is an exothermic reaction as is the oxidation of HBr with $H_2O_2$. To control the reaction mass temperature, it may become necessary to remove heat from the reaction mass. Heat removal can be effected by running the reaction at reflux with the condenser facilitating the heat removal. If it is desired to operate at a temperature below the atmospheric boiling point of the reaction mixture, the reaction can be run under sub-atmospheric pressure.

Generally, the basic concepts of the processes of this invention are not appreciably affected by the process pressure. Thus, the process can be run under sub-atmospheric, atmospheric or super-atmospheric pressure.

The reactor used in the practice of this invention is preferably a continuously stirred tank reactor. The reaction mass is being continuously formed and a portion thereof is being removed from the reactor during the reaction mass formation. The reactor design should be such that the average residence time in the reactor is sufficient to ensure tetrabromination of substantially all of the bisphenol-A and/or underbrominated bisphenol-A. Terms such as "continuous feed" and "continuous withdrawal" and terms of analogous import are not meant to exclude interrupted feeds or withdrawals. Generally, such interruptions are of short duration and may be suitable depending upon the scale and design of the reactor. For example, since the tetrabromobisphenol-A precipitate will tend to settle near the bottom of the reactor, a withdrawal may be made and then stopped for a period of time to allow for precipitate build-up to occur prior to the next withdrawal. Such a withdrawal is to be considered continuous in the sense that the withdrawal does not await the completion of the reactor feeds as is characteristic of batch processes. Uninterrupted withdrawal is preferred, however.

Experimental evidence available to date indicates that the preferred reactor residence time should be within the range of from about 30 to about 150 minutes when using a stirred-tank reactor and the process conditions which are preferred for that operating mode. Reactor residence time, as used herein, is the reactor volume divided by the flow rate at which slurry is removed from the reactor.

Workup of the reaction mass being continuously or at least substantially continuously withdrawn from the reactor is not complicated. Since the water content of the reaction mass is so large and since the tetrabromobisphenol-A is so insoluble in the presence of such an amount of water, there may only be a small benefit in rapidly cooling the withdrawn reaction mass upon its withdrawal from the reactor. The benefit of cooling resides mainly in reducing the vapor pressure of solvated gaseous bromides, e.g.,., methyl bromide or ethyl bromide, in the withdrawn reaction mass prior to the liquid-solids separation. There also may possibly be some reduction in rate of continued formation of these alkyl bromides. In addition, depending upon the water content of the reaction mass, cooling may allow for additional precipitation of tetrabromobisphenol-A from the reaction mass. Additionally, depending on the separation technique used, cooling the reaction mass may make it easier to handle downstream from the reactor. Thus, if none of these features are of concern or relative value, then the reaction mass can be subjected to liquid-solids separation as soon as it can be transported to the separation equipment. If, however, cooling is desired, the cooling time will depend upon how the reaction mass is to be cooled and to what temperature it is to be cooled. In a laboratory setting, cooling times can range from about one minute to about thirty minutes.

Before subjecting the withdrawn reaction mass to liquid-solids separation additional water may be added to the reaction mass to ensure that even more tetrabromobisphenol-A precipitate is formed in the reaction mass. The water addition and precipitation time can be very short, e.g, less than about thirty minutes. Use of cool water will also have the effect of reducing the temperature of the reaction mass being treated.

The liquid-solids separation is readily conducted by use of such techniques as decantation, centrifugation, filtration or similar physical separation procedures. After the recovery of the solids from the liquid, the solids are preferably washed with a solution of water and the particular water-miscible organic solvent used in the reaction. The washing removes essentially all the mother liquor from the solids. The mother liquor typically contains impurities such as tribromophenol, HBr, and hydrolyzable impurities. A typical wash can be a 30 wt % methanol or ethanol in water solution. The washed solids are then rewashed with deionized water to remove any remaining water-miscible organic solvent from the first wash so as to minimize emission problems when drying the product.

Individual or combined workup operations on the withdrawn reaction mass and on the recovered tetrabromobisphenol-A can be conducted on a batch, semi-continuous, or continuous basis, as desired.

At process initiation for plant startup, it is desirable to charge the reactor with a liquid pre-reaction charge which will become a part of the reaction mass upon the commencement of the concurrent feeds. The liquid charge will provide a stirrable reaction mass and act as a heat sink to moderate temperature changes in the reaction mass. The liquid charge is preferably comprised of water and the same water-miscible organic solvent that is to be fed in the bisphenol-A and/or underbrominated bisphenol-A solution or slurry. It is preferred that the liquid charge be acidic, e.g., containing from 1 to 20 wt % acid such as HBr, HCl, or the like. The acid seems to promote good color in the initial tetrabromobisphenol-A produced. Further, during process initiation it is preferred that the solvent be saturated with solvated tetrabromobisphenol-A. It is also preferred that the reactor be charged with seed particles of tetrabromobisphenol-A during plant startup. The saturation of the solvent and the presence of the seed particles both act to enhance the precipitation of the tetrabromobisphenol-A produced during the bromination during process initiation. It is most practical to use a heel from a discontinued prior operation as the liquid charge. The tetrabromobisphenol-A seed particles can be brought over in the reaction mass from a previous discontinued operation, or even from a suitable batch operation. Alternatively, the seed particles can be added separately to the heel. If a heel is not available, it is also possible to use a separate water and water-miscible organic solvent feed, which are a part of the total solution feed, to form the initial liquid charge. In this scheme, an initial amount of water and water-miscible organic solvent are fed to the reactor prior to the initiation of the solvated bisphenol-A portion and/or the slurry of underbrominated bisphenol-A portion of the solution or slurry feed. The only caveat to this scheme is that there must be apportionment of the various feeds making up the solution feed so that there will still be compliance with the various parameters which define the processes of this invention.

Product of excellent quality can be produced pursuant to this invention. The tetrabromobisphenol-A product can have a purity of 97 wt % and above, and with a very small tribromobisphenol-A content, if any, of about 2 wt % or less. Moreover, it is possible to produce tetrabromobisphenol-A product having an APHA color less than about 50 (as determined by dissolving 80 grams of tetrabromobisphenol-A product in 100 mL of acetone). Hydrolyzable bromides can also be kept low, generally below about 60 ppm. The process yields are impressive, with yields within the range of from about 95 to about 99% being possible.

As can be appreciated from the foregoing, the water content of the solvent, the reaction temperature, and the HBr and $Br_2$ contents in the reaction mass during the bisphenol-A and/or underbrominated bisphenol-A feed all contribute to obtaining the desired tetrabromobisphenol-A product in an efficient manner. The selection of particular values for each of these process parameters to obtain the results desired will depend on the desired output and needs in respect of a particular plant operation and upon the equipment available. One plant design may emphasize one benefit of using a process of this invention over other possible benefits. Thus, designers of that plant and its process may select different process parameter values than those selected by the designers of another plant in order to emphasize one or more other benefits.

Though preferably designed to minimize the production of methyl bromide or ethyl bromide coproduct, the processes of this invention are readily adaptable to modification to coproduce methyl bromide or ethyl bromide.

While the foregoing descriptions of the oxidation of HBr generally speak of the HBr being oxidized in the reactor or reaction mass, it is within the scope of the processes of this invention to also remove HBr from the reactor and oxidize it outside of the reactor (i.e., in another suitable closed vessel or like apparatus) and then to send the so-produced $Br_2$ back to the reactor, or to separately generate bromine needed for the process by operation of a separate installation wherein HBr from one or more other sources is oxidized to bromine.

HBr fed to the reactor can be either recycled HBr recovered from the off-gases of the bromination reaction, or non-indigenous HBr obtained from other sources, or a combination of both such sources.

To achieve the greatest benefits made possible by this invention one should, to the extent practicable under the particular set of operating parameters being used, arrange to reach the steady-state operating conditions as described herein with as little delay as is feasible. And once those conditions have been reached they should be maintained as long as is practicable during the bromination. An advantage of the present continuous mode of operation is that once the steady-state of operation within these conditions has been reached, it is possible to maintain them as long as is desired. In such case reaction mass and precipitate formed during the startup phases of the operation prior to reaching the selected steady-state conditions can be discarded.

The following Examples are presented to illustrate the practice of, and advantages made possible by, this invention.

These Examples are not intended to limit, and should not be construed as limiting, the scope of this invention to the particular operations or conditions described therein. The APHA color values set forth in these Examples were determined by dissolving 80 grams of the tetrabromobisphenol-A product in 100 mL of acetone.

EXAMPLE 1

A 1-liter flask was equipped with a mechanical stirrer, condenser, thermometer, and a down-drain to continually remove slurry from the reactor. The flask was fitted with three feed tubes (one-eighth inch O.D.) for feeding bisphenol-A solution, 48% HBr solution and 50% $H_2O_2$ solution. The top of the condenser was connected to a vacuum pump. The temperature of the reactor was maintained at about 60° C. by controlling the vacuum at about 26 inches of Hg. Bisphenol-A, HBr and $H_2O_2$ solutions were fed to the reactor using peristaltic pumps. The bisphenol-A solution was prepared by dissolving 800 grams of bisphenol-A in 3200 grams of ethanol. A 50 wt % aqueous solution (200 mL) of ethanol was charged to the reactor as the heel. The above bisphenol-A solution, and 50 wt % aqueous $H_2O_2$ and 48 wt % aqueous HBr solutions were fed to the reactor at flow rates of about 13.0 mL/min., 1.9 mL/min. and 8.0 mL/min., respectively. HBr and $H_2O_2$ feeds were kept stoichiometrically ahead of the bisphenol-A feed and as a result, the reaction mass was pale yellow. The temperature of the reactor rose to about 60° C. and was kept at that temperature by reflux cooling. The product slurry was continually drained from the bottom of the reactor to keep a constant level in the reactor. The slurry was filtered and washed first with 30 wt % aqueous ethanol and then with deionized water. The washed precipitate was dried and analyzed. The product tetrabromobisphenol-A had APHA color of 30 and a purity of 99.4%. The mother liquor contained 14.1% HBr and 0.8% $Br_2$.

EXAMPLE 2

The reactor flask was fitted with a dip tube for feeding bromine vapor and three feed tubes which terminated in the vapor phase, for feeding bisphenol-A solution, 48 wt % HBr solution and 50 wt % $H_2O_2$ solution. The bromine tube from the pump was connected to a nitrogen inlet and a bromine vaporizer and a gas outlet were connected to the diptube in the reactor. A 50 wt % aqueous solution (200 mL) of ethanol was charged to the reactor as the heel. A 20 wt % solution of bisphenol-A in ethanol, the 50 wt % aqueous $H_2O_2$ solution, the 48 wt % aqueous HBr solution, and $Br_2$ were fed concurrently to the reactor at flow rates of about 9.0 mL/min., 1.5 mL/min., 7.5 mL/min. and 0.7 mL/min., respectively. The temperature of the pale yellow slurry rose to about 60° C. and was kept at that temperature by reflux cooling. The product slurry was continually drained to keep a constant level in the reactor. The slurry was filtered and washed first with 30 wt % aqueous ethanol and then with deionized water. The precipitate was dried and analyzed. The product tetrabromobisphenol-A had a purity of 99.8% and an APHA color of 25.

It is to be understood that the processes of this invention can be run in combination with processes having process parameters not of this invention. For example, if it is desired to produce an intermediate amount of methyl bromide ethyl bromide, a process similar to a process described above using methanol or ethanol as the water-miscible organic solvent but with process parameters which promote the formation of methyl bromide or ethyl bromide, such as, for example, use of a low water content in the vicinity of about 10 wt %. This process could be run for a period of time and then could be interrupted with the imposition of the parameters of this invention so as to diminish methyl bromide or ethyl bromide production. In this way, the methyl bromide or ethyl bromide production can be controlled within desired production limits by combining both processes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for producing tetrabromobisphenol-A, which process comprises providing a liquid phase reaction system in which there is directly formed a tetrabromobisphenol-A precipitate by the bromination of bisphenol-A and/or under-brominated bisphenol-A using an excess of bromine over the stoichiometric amount theoretically required to produce tetrabromobisphenol-A, more than 50 mole percent of the bromine in the reaction system being generated in situ by oxidizing HBr, at least part of which HBr is continuously fed to said reaction system as HBr.

2. A process of claim 1 wherein the HBr that is continuously fed to said reaction system is fed as aqueous hydrobromic acid.

3. A process of claim 1 wherein HBr co-product is also oxidized in situ to bromine.

4. A process of claim 1 wherein the bromination is conducted in the presence of an amount of HBr that is high enough to protect the tetrabromobisphenol-A being produced from excessive color development.

5. A process of claim 1 wherein the bromination is conducted at such rate that (i) there is insufficient opportunity for significant precipitation of the intermediate, tribromobisphenol-A, to occur, and (ii) while the bisphenol-A and/or underbrominated bisphenol-A is/are being brought into contact with unreacted bromine in the liquid phase of the reaction mass, tetrabromobisphenol-A is being produced substantially continuously.

6. A process of claim 5 wherein the yield of the tetrabromobisphenol-A as it is being produced substantially continuously is at least about 90% based on the amount of the bisphenol-A and/or underbrominated bisphenol-A already fed.

7. A process of claim 6 wherein said yield is at least about 95%.

8. A process of claim 1 wherein the tetrabromobisphenol-A produced has an APHA color of less than about 100, the APHA color being determinable by dissolving 80 grams of the tetrabromobisphenol-A product in 100 mL of acetone.

9. A process of claim 1 wherein the HBr that is continuously fed to said reaction system is fed as aqueous hydrobromic acid; wherein HBr co-product is also oxidized in situ to bromine; wherein the bromination is conducted in the presence of an amount of HBr that is high enough to protect the tetrabromobisphenol-A being produced from excessive color development; wherein the bromination is conducted at such rate that (i) there is insufficient opportunity for significant precipitation of the intermediate, tribromobisphenol-A, to occur, and (ii) while the bisphenol-A and/or underbrominated bisphenol-A is/are being brought into contact with unreacted bromine in the liquid phase of the reaction mass, tetrabromobisphenol-A is being produced substantially continuously; and wherein the yield of the tetrabromobisphenol-A as it is being produced substantially continuously is at least about 90% based on the amount of the bisphenol-A and/or underbrominated bisphenol-A fed.

10. A process of claim 9 wherein the tetrabromobisphenol-A produced has an APHA color of less than about 100, the APHA color being determinable by dissolving 80 grams of the tetrabromobisphenol-A product in 100 mL of acetone.

11. A process of claim 9 wherein said yield is at least about 95%.

12. A process of claim 10 wherein said yield is at least about 95%.

13. A process of claim 8 wherein said APHA color is 50 or less.

14. A process of claim 10 wherein said APHA color is 50 or less.

* * * * *